United States Patent [19]
Ek et al.

[11] Patent Number: 5,730,747
[45] Date of Patent: Mar. 24, 1998

[54] SUTURE PASSING FORCEPS

[75] Inventors: Steven W. Ek, Bolton; Richard E. Walton, North Andover, both of Mass.

[73] Assignee: Smith & Nephew, Inc., Andover, Mass.

[21] Appl. No.: 603,859

[22] Filed: Feb. 22, 1996

Related U.S. Application Data

[63] Continuation-in-part of Ser. No. 479,514, Jun. 7, 1995, abandoned.

[51] Int. Cl.⁶ .................................................. A61B 17/04
[52] U.S. Cl. ................................................. 606/148; 606/139
[58] Field of Search ..................................... 606/139, 144, 606/145, 146, 147, 148, 222, 223, 224

[56] References Cited

U.S. PATENT DOCUMENTS

| | | |
|---|---|---|
| 919,138 | 4/1909 | Drake et al. . |
| 1,635,066 | 7/1927 | Wells . |
| 1,815,725 | 7/1931 | Pilling et al. . |
| 2,610,631 | 9/1952 | Calicchio . |
| 2,880,728 | 4/1959 | Rights . |
| 3,013,559 | 5/1961 | Thomas . |
| 3,349,772 | 10/1967 | Rygg . |
| 3,470,875 | 10/1969 | Johnson . |
| 3,638,653 | 2/1972 | Berry . |
| 3,752,516 | 8/1973 | Mumma . |
| 3,840,017 | 10/1974 | Violante . |
| 3,842,840 | 10/1974 | Schweizer . |
| 3,871,379 | 3/1975 | Clarke . |
| 3,901,244 | 8/1975 | Schweizer . |
| 3,946,740 | 3/1976 | Bassett . |
| 4,161,951 | 7/1979 | Scanlan, Jr. . |
| 4,164,225 | 8/1979 | Johnson et al. . |
| 4,224,947 | 9/1980 | Fukuda . |
| 4,312,337 | 1/1982 | Donohue . |
| 4,493,323 | 1/1985 | Albright et al. . |
| 4,596,249 | 6/1986 | Freda et al. . |
| 4,602,635 | 7/1986 | Mulhollan et al. . |
| 4,621,640 | 11/1986 | Mulhollan et al. . |
| 4,641,652 | 2/1987 | Hutterer et al. . |
| 4,643,178 | 2/1987 | Nastari et al. . |
| 4,779,616 | 10/1988 | Johnson . |
| 4,781,190 | 11/1988 | Lee . |
| 4,890,615 | 1/1990 | Caspari et al. . |
| 4,923,461 | 5/1990 | Caspari et al. . |
| 4,957,498 | 9/1990 | Caspari et al. . |
| 4,961,741 | 10/1990 | Hayhurst . |
| 5,084,058 | 1/1992 | Li . |
| 5,087,263 | 2/1992 | Li . |

(List continued on next page.)

FOREIGN PATENT DOCUMENTS

WO 95/02363  1/1995  European Pat. Off. .

OTHER PUBLICATIONS

PCT Search Report dated 29 Aug. 1996.
PCT Written Opinion dated Jun. 19, 1997.
Smith & Nephew Dyonics, Product Advertisement for PRO-LINE Reusable Endoscopic Hand Instruments.
Auto Suture Company, Product Advertisement, "Endoscopic suturing made easy", 1994.

*Primary Examiner*—Michael Buiz
*Assistant Examiner*—Patrick W. Rasche
*Attorney, Agent, or Firm*—Fish & Richardson P.C.

[57] ABSTRACT

A suture passing forceps includes an axially elongated support shaft, and a first suture holder for removably holding a needled suture and a second suture holder for capturing the needled suture. The first suture holder includes a suture inlet through which at least part of the suture can be passed. The first suture holder or the second suture holder is an actuatable member which pivots toward an operating position to capture the needled suture in the second suture holder and pivots away from the operating position to remove the suture from the first suture holder. The suture inlet in the suture holder enables complete removal of the suture from the suture holder when the actuatable member and the needled suture move away from the operating position. The second suture holder includes a holding region defined by a contoured surface permitting the needled suture to slide within the holding region.

24 Claims, 10 Drawing Sheets

U.S. PATENT DOCUMENTS

| | | |
|---|---|---|
| 5,100,415 | 3/1992 | Hayhurst . |
| 5,100,418 | 3/1992 | Yoon et al. . |
| 5,100,421 | 3/1992 | Christoudias . |
| 5,133,723 | 7/1992 | Li et al. . |
| 5,149,329 | 9/1992 | Richardson . |
| 5,163,946 | 11/1992 | Li . |
| 5,176,691 | 1/1993 | Pierce . |
| 5,181,919 | 1/1993 | Bergman et al. . |
| 5,192,287 | 3/1993 | Fournier et al. . |
| 5,201,744 | 4/1993 | Jones . |
| 5,217,471 | 6/1993 | Burkhart . |
| 5,222,508 | 6/1993 | Contarini . |
| 5,224,955 | 7/1993 | West ............................................. 606/226 |
| 5,234,443 | 8/1993 | Phan et al. . |
| 5,234,444 | 8/1993 | Christoudias . |
| 5,250,054 | 10/1993 | Li . |
| 5,250,055 | 10/1993 | Moore et al. . |
| 5,257,637 | 11/1993 | El Gazayerli . |
| 5,259,846 | 11/1993 | Granger et al. ........................... 606/224 |
| 5,261,917 | 11/1993 | Hasson et al. . |
| 5,269,783 | 12/1993 | Sander ....................................... 606/72 |
| 5,269,791 | 12/1993 | Mayzels et al. . |
| 5,281,234 | 1/1994 | Wilk et al. . |
| 5,382,257 | 1/1995 | Lewis et al. ............................... 606/148 |
| 5,387,221 | 2/1995 | Bisgaard ..................................... 606/148 |
| 5,389,103 | 2/1995 | Melzer et al. .............................. 606/144 |
| 5,417,712 | 5/1995 | Whittaker et al. ........................ 606/232 |
| 5,454,823 | 10/1995 | Richardson et al. ...................... 606/148 |
| 5,571,090 | 11/1996 | Sherts ........................................ 606/145 |
| 5,578,044 | 11/1996 | Gordon et al. . |
| 5,645,552 | 7/1997 | Sherts ........................................ 606/145 |

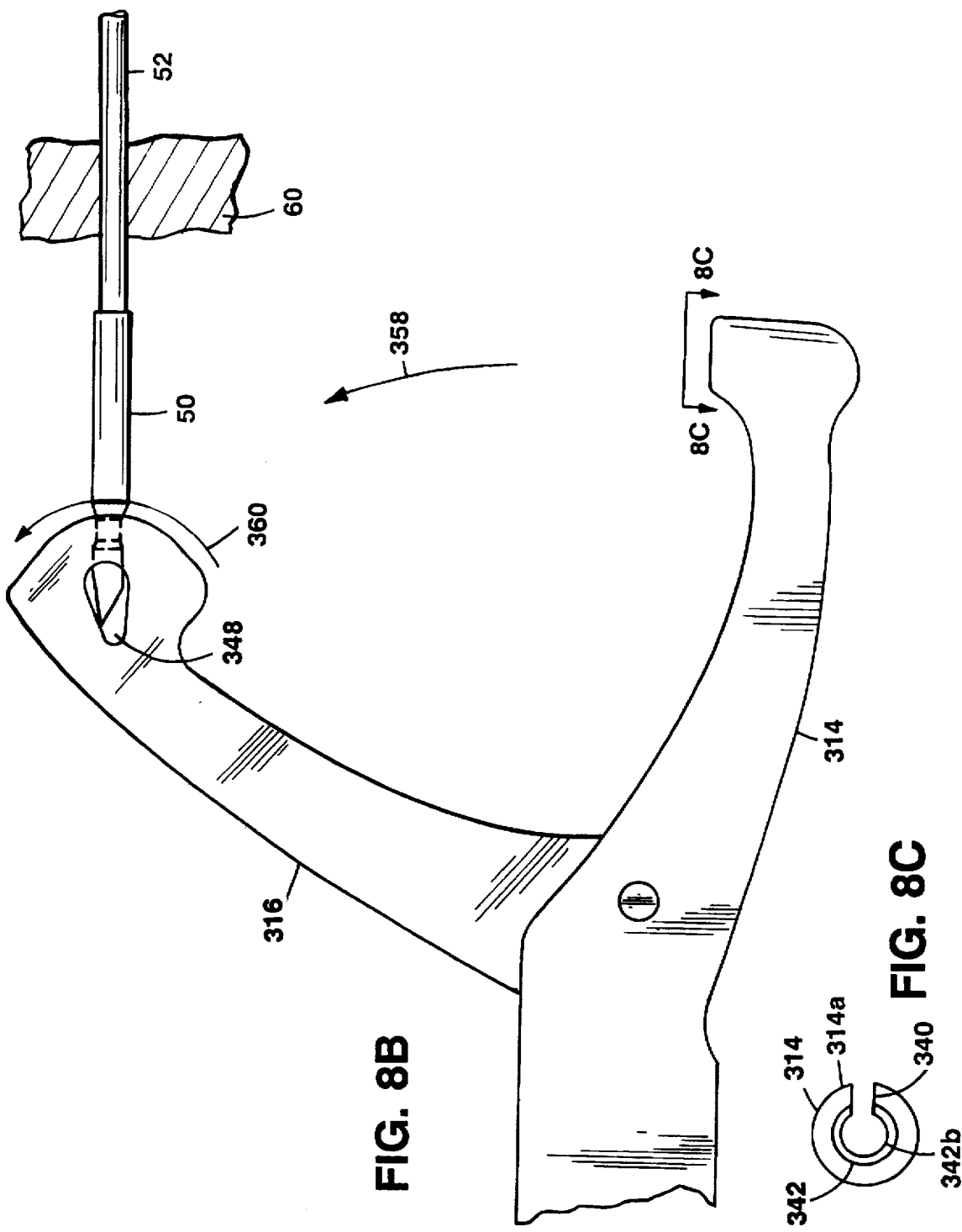

5,730,747

1
SUTURE PASSING FORCEPS

This is a continuation-in-part of application Ser. No. 08/479,514, filed on Jun. 07, 1995, now abandoned.

BACKGROUND OF THE INVENTION

The invention relates generally to suture forceps, and more particularly, to a method and apparatus for passing needled sutures.

Current suturing instruments can include upper and lower jaws with a needle associated with the lower jaw. The jaws are used to punch the needle through the tissue to be sutured and a suture thread is then fed through the needle, passing the suture thread from the lower jaw to the upper jaw. Other suturing instruments have been known in which a needle is pushed out of a lower jaw and through tissue, passed to an upper jaw, and held in place in the upper jaw with a spring.

SUMMARY OF THE INVENTION

The invention relates to a suture passing forceps. The invention features an axially elongated support shaft, and a suturing assembly at a distal end of the support shaft. The suturing assembly includes a first suture holder supported by the support shaft for removably holding a needled suture, and a second suture holder supported by the support shaft for passively capturing the needled suture. The suture holder includes a suture inlet through which at least part of the suture can be passed. The first suture holder or the second suture holder is an actuatable member which pivots toward an operating position to passively capture the needled suture in the second suture holder and pivots away from the operating position to remove the suture from the first suture holder. The suture inlet in the suture holder enables complete and free removal of the suture from the suture holder when the actuatable member and the needled suture move away from the operating position.

In particular embodiments of the invention, the second suture holder is the actuatable member. The first suture holder includes a holding region for removably holding a needle of the needled suture. The first suture holder includes a jaw and the suture inlet is defined by a slot of a selected width in the jaw through which a suture thread of the needled suture can pass, the holding region being defined by an enlarged section of the slot into which the needle of the needled suture can be placed. The holding region is oriented at an angle of about 90 degrees to an axis of the support shaft and the enlarged section of the slot is oriented to hold the needle at an outward angle of about 5 to 10 degrees to an axis normal to a longitudinal axis of the shaft to better engage the tissue to be sutured.

In the illustrated embodiment, the second suture holder includes a holding region having a spring force for removably holding a needle of the needled suture. In accordance with the invention, the second holding region defines a passive spring fit. The second suture holder includes a jaw having a slot of a selected width, the holding region being defined by an enlarged section of the slot and into which at least a portion of the needle can be spring fit, the relative sizes of the needle and the enlarged section of the second holding region defining, in part, the spring force.

The suture passing forceps include a handle at a proximal end of the support shaft, the handle being actuatable to move the actuatable member toward and away from its operating position.

In one illustrated embodiment, the second suture holder includes a window enabling a user to confirm that the suture has been passed from the first suture holder to the second suture holder.

2

In another illustrated embodiment, the first and second suture holders include inner surfaces that aid in preventing tissue hang-up thereon.

In accordance with the invention, a needled suture includes a suture thread and a sharp-tipped needle attached to a least one end of the suture thread. The needle includes a substantially straight body co-axially aligned with the suture thread. The body includes a holding portion having a different cross-sectional profile than portions of the body surrounding the holding portion. The body is substantially tubular-shaped. The needled has a length of less than about 0.5 inches.

According to another aspect of the invention, a suture anchor assembly includes an anchor for attachment to bone; at least one needled suture for use with the anchor, the needled suture including a suture thread and a substantially straight, sharp-tipped needle attached to a least one end of the suture thread. The needle includes a holding portion having a different cross-sectional profile than portions of the needle surrounding the holding portion. The suture thread may have a needle attached at each end.

A method of suturing, in accordance with the invention, includes the steps of punching a distal end of a needle of a needled suture through tissue to be sutured at a suture site thus creating a hole through the tissue through which a suture thread of the needled suture can pass; grabbing the distal end of the needle in a passive spring fit; moving the actuatable member away from the tissue being sutured to pull the suture thread through the suture hole without engaging a distal end of the suture thread; and removing only a needled end of the needled suture from the suture site by withdrawing the actuating member.

In accordance with the method of the invention, the punching is facilitated by actuation of the actuatable member pivoting toward its operating position. The needle is held in a suture holder during punching of the distal end of the needle through the tissue, the method including removing the needle from the suture holder by the action of grabbing the distal end of the needle with the actuatable member.

A method of minimally-invasively suturing deep tissue through a portal includes anchoring a suture thread having a needle attached thereto at each end to a suture anchor, suturing a first tissue using a first of the needled ends of the suture thread, and suturing a second tissue using a second of the needled ends of the suture thread, the suture thread, during both suturing steps, always being anchored to the suture anchor.

According to another aspect of the invention, a suture passing forceps includes an axially elongated support shaft, and a suturing assembly at a distal end of the support shaft. The suturing assembly includes a first suture holder supported by the support shaft for removably holding a needled suture, and a second suture holder supported by the support shaft for capturing the needled suture. The suture holder includes a suture inlet through which at least part of the suture can be passed. The first suture holder or the second suture holder is an actuatable member which pivots toward an operating position to capture the needled suture in the second suture holder and pivots away from the operating position to remove the suture from the first suture holder. The second suture holder includes a holding region partially defined by a contoured surface permitting the needled suture to slide within the holding region.

In particular embodiments of this aspect of the invention, the second suture holder is the actuatable member. The contoured surface is configured to facilitate removal of the needled suture from the holding region. The first suture holder includes a jaw and the suture inlet is defined by a slot of a selected width in the jaw through which a suture thread of the needled suture can pass. A needle holding region is defined by an enlarged section of the slot and a first portion of the enlarged section has a diameter greater than a diameter of the needle of the needled suture and a second portion of the enlarged section has a diameter less than the diameter of the needle. The slot is of limited depth extending from a surface of the jaw to the enlarged section.

According to another aspect of the invention, a method of suturing includes the steps of punching a distal end of a needle of a needled suture through tissue to be sutured at a suture site thus creating a hole through the tissue through which a suture thread of the needled suture can pass; grabbing the distal end of the needle within a holding region in a first suture holder; pulling the suture through the suture hole without engaging a distal end of the suture thread; removing only a needled end of the needled suture from the suture site; and removing the needled suture from the first suture holder by sliding the needled suture along a contoured surface of the holding region.

In accordance with this aspect of the invention, the punching is facilitated by actuation of the suture holder pivoting toward its operating position. The needle is held in a second suture holder during punching of the distal end of the needle through the tissue and the method includes removing the needle from the second suture holder by the action of grabbing the distal end of the needle with the first suture holder and moving the first suture holder away from the tissue. The distal end of the needle is grabbed in a passive spring fit within the holding region.

BRIEF DESCRIPTION OF THE DRAWINGS

Other objects, features and advantages of the invention will be apparent from the following description taken together with the drawings in which:

FIG. 8B shows the suturing assembly of FIG. 8 in a second operative position; and FIG. 8C is an end view of a suture holder of FIG. 8B, taken along lines 8C—8C.

DESCRIPTION OF THE PREFERRED EMBODIMENTS

Figure 1:
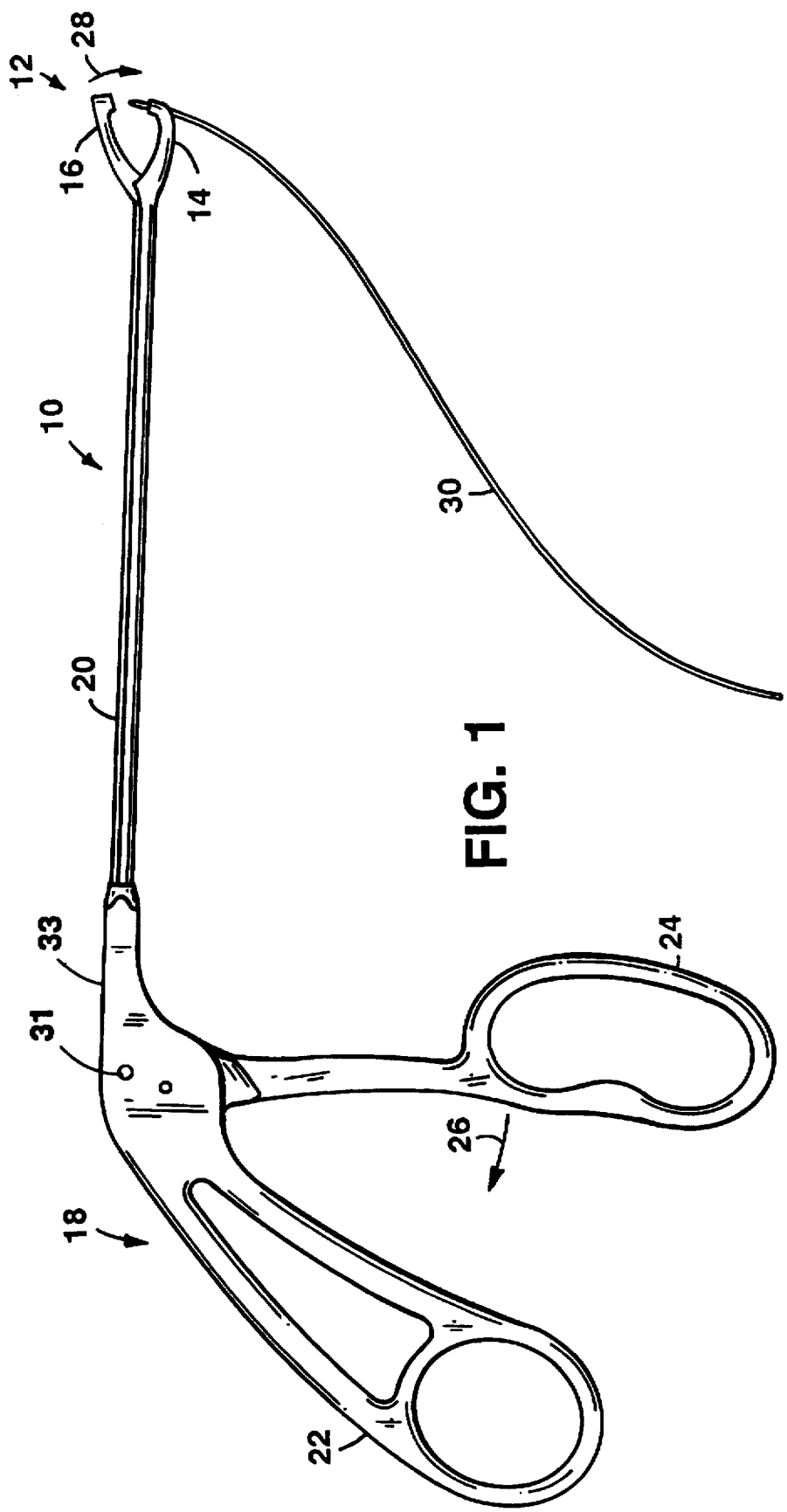
FIG. 1 shows the suture passing forceps of the invention with a needled suture.

Referring to FIG. 1, according to the invention, a suture passing forceps 10 for use, e.g., in arthroscopic and endoscopic procedures, includes a suturing assembly 12 having a suture holder 14 for removably holding a needled suture 30, and an actuatable member 16. Actuatable member 16 is pivotably supported by a support shaft 20. A handle 18 connected to support shaft 20 is used to actuate actuatable member 16. Handle 18 includes a stationary thumb section 22 and a movable finger section 24. Movement of finger section 24 in the direction of an arrow 26 moves actuatable member 16 in the direction of an arrow 28 to an operating position adjacent the suture holder 14 (FIG. 2a). The reverse motion of finger section 24 returns actuatable member 16 to its original position. An actuation mechanism such as used in the Smith & Nephew Dyonics 2.7 mm. Scoop, product #7204665, may be used. Suture passing forceps 10 include a suture tie off post 31, for example, a pin with an o-ring placed between a head of the pin and body 33 of forceps 10. While the illustrated embodiment shows suture holder 14 as stationary and actuatable member 16 pivotably mounted, suture holder 14 can be pivotably mounted and actuatable member 16 stationary.

Figure 2:
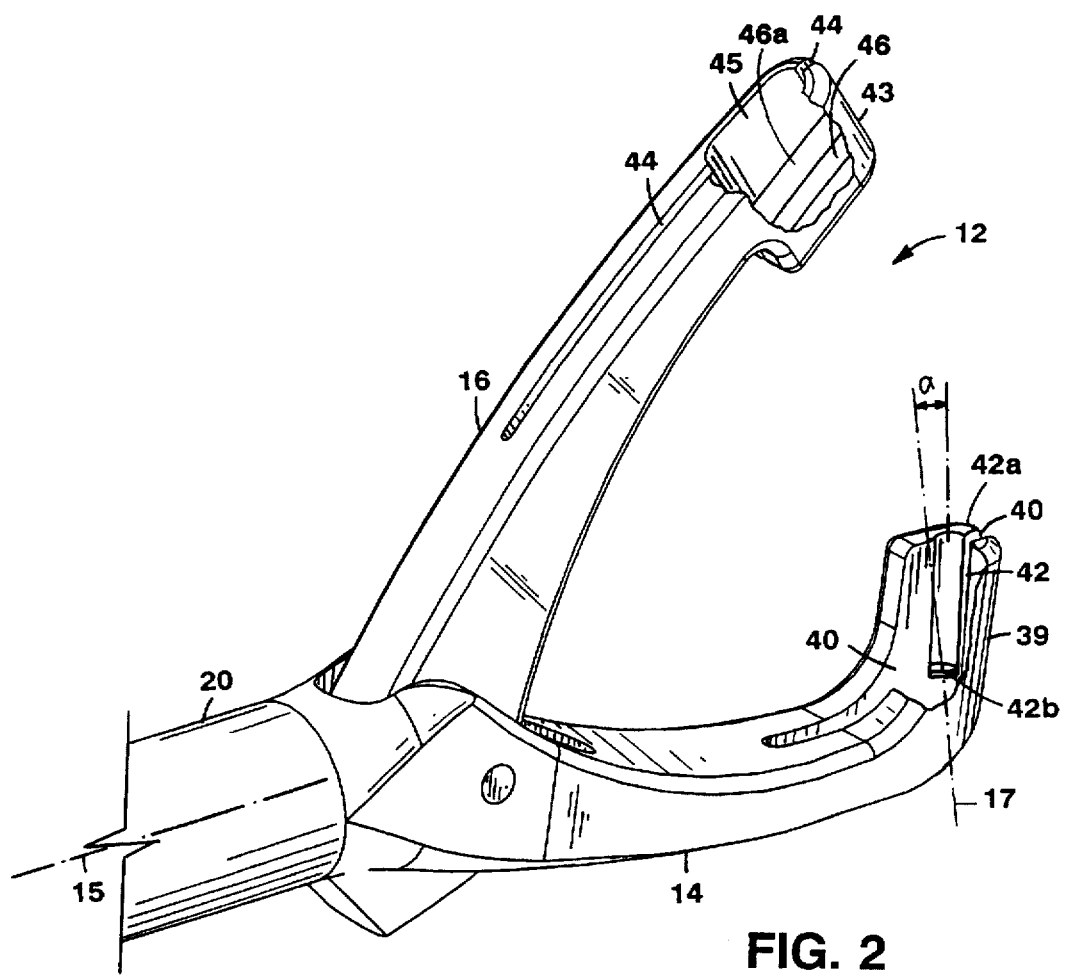
FIG. 2 is a partially cut-away perspective view of the suturing assembly of the suture passing forceps of FIG. 1 shown in an open position.
Figure 2A:
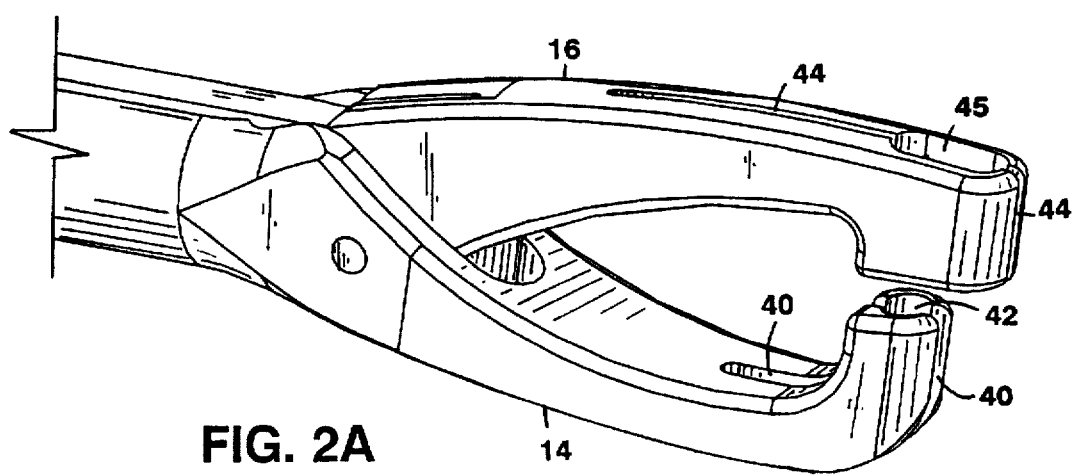
FIG. 2A is a perspective view of the suturing assembly of FIG. 1 shown in a closed position.

Referring to FIGS. 2 and 2A, suture holder 14 includes a jaw 39 with a suture inlet slot 40 and a needle holding region 42 for removably holding a needle of needled suture 30. Needle holding region 42 is defined by an enlarged area of slot 40 which extends from a distal end 42a of jaw 39 to a ledge 42b. Slot 40 cuts through the entire region of jaw 39. Jaw 39 is oriented so that its axis 17 is about 90 degrees to a longitudinal axis 15 of support shaft 20. Holding region 42 is oriented to hold a needle of needled suture 30 at an angle α of about 5 to 10 degrees from axis 17 of jaw 39 to better enable a needle to engage the tissue to be sutured. As will be described in more detail below, slot 40 enables complete removal of needled suture 30 from suture holder 14 after passage of the needled suture through tissue. Actuatable member 16 includes a jaw 43 with a slot 44 having enlarged section 45 with a needle holding region 46 of smaller width than enlarged section 45. A ledge 46a in enlarged section 45 defines needle holding region 46.

A suture needle can be removably held within suture holding region 42 of jaw 39. Slot 40 has a width of, e.g., about 0.021"; holding region 42 has a diameter of, e.g., about 0.034–0.035"; and needle 50 (see FIG. 3) has a diameter of, e.g., about 0.0315"–0.0335". Needle 50 rests against ledge 42b of holding region 42 and suture thread 52 (see FIG. 4) passes through slot 40 and is tied off on post 31. Alternatively, holding region 42 can sized to produce a spring fit with needle 50. Needle 50 can be held within holding region 46 of jaw 43 by the force of a passive spring fit. The relative sizes of the diameter or size of holding region 46 and the diameter of needle 50 in combination with the spring constant associated with the material of the jaw 43 define the spring force with which needle 50 is held within holding region 46. Slot 44 has a width of, e.g., about 0.01"; holding region 46 has a width of, e.g., about 0.021"–0.026" and a length of, e.g., about 0.06"; and a crimped area of the needle 50, described further below, has a width of, e.g., about 0.025"–0.027". The holding force of actuatable member 16 on the needle is greater than the holding force of suture holder 14 on the needle. This difference in holding force enables the needle to be passed from suture holder 14 to actuatable member 16, as described below.

Figure 3:
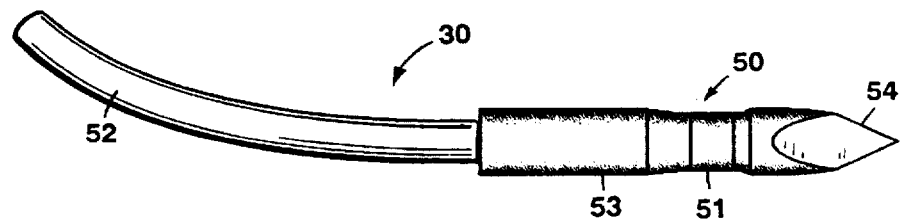
FIG. 3 shows a needled suture for use with the suture passing forceps of FIG. 1.

Referring to FIG. 3, needled suture 30 for use with suture passing forceps 10 includes a needle 50 co-axially aligned with suture thread 52 and attached, e.g., by crimping or clamping, to suture thread 52 at an attachment area 51. Needle 50 includes a substantially straight, tubular shaped body 53 and a pointed distal tip 54 for ease of passage through tissue. The length of needle 50 is less than about 0.5" and preferably about 0.3". It is the attachment area 51 that is held by holding region 46 of actuatable member 16. Suture thread 52 may be, e.g., #1 or #2 size sutures, monofilament or braided.

Figure 4:
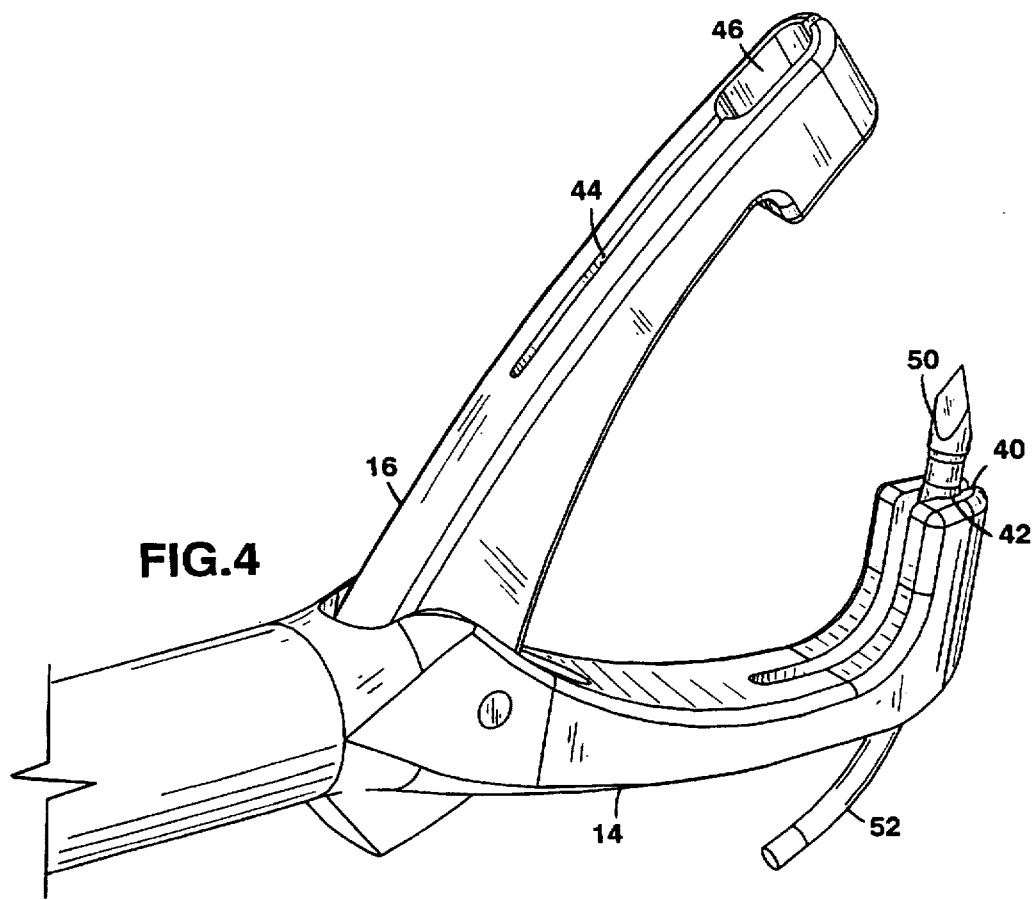
FIG. 4 shows the suturing assembly of FIG. 2 with the needled suture of FIG. 3.
Figure 4A:
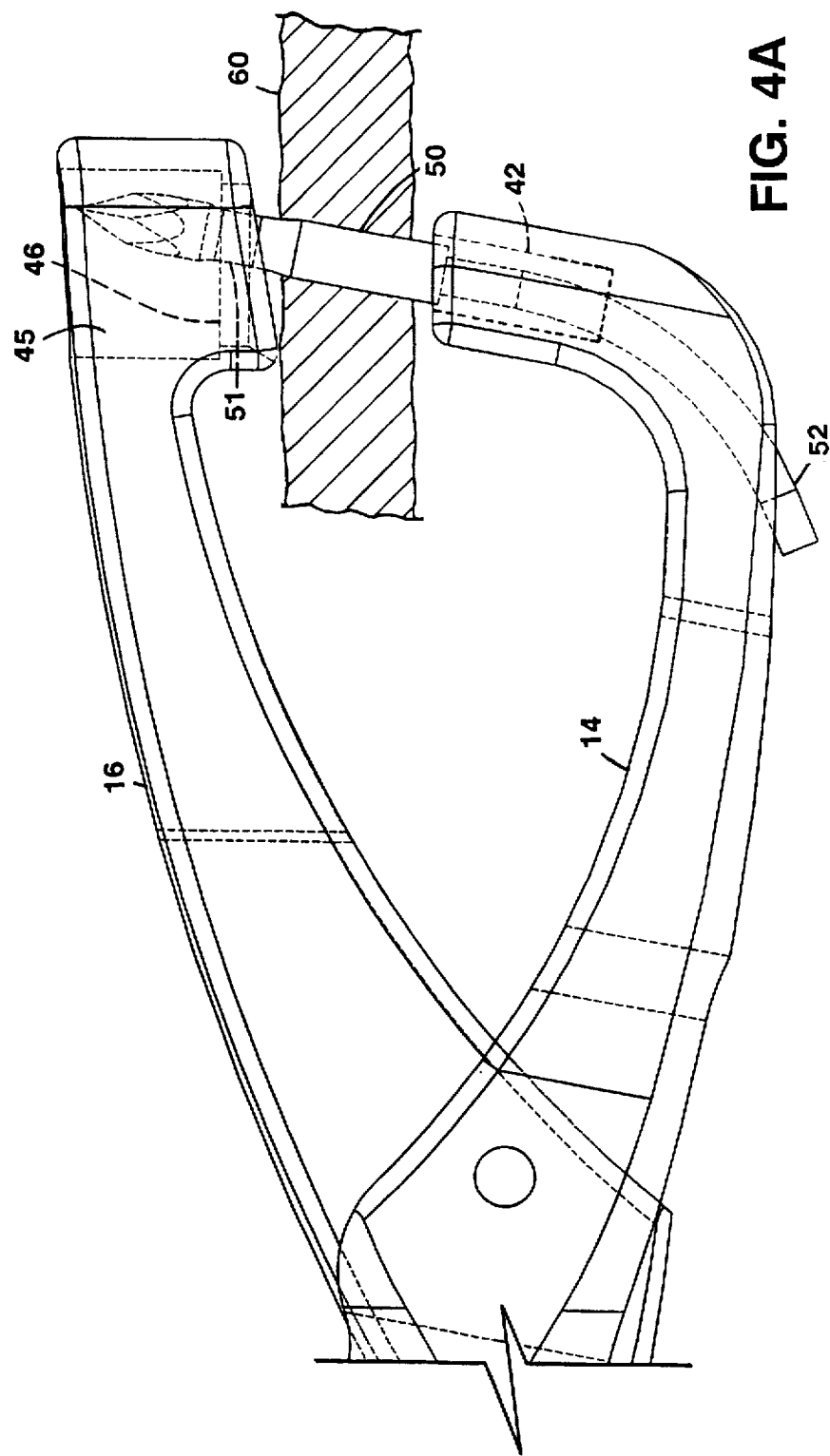
FIG. 4A shows the suturing assembly of FIG. 4 in a first operative position.
Figure 4B:
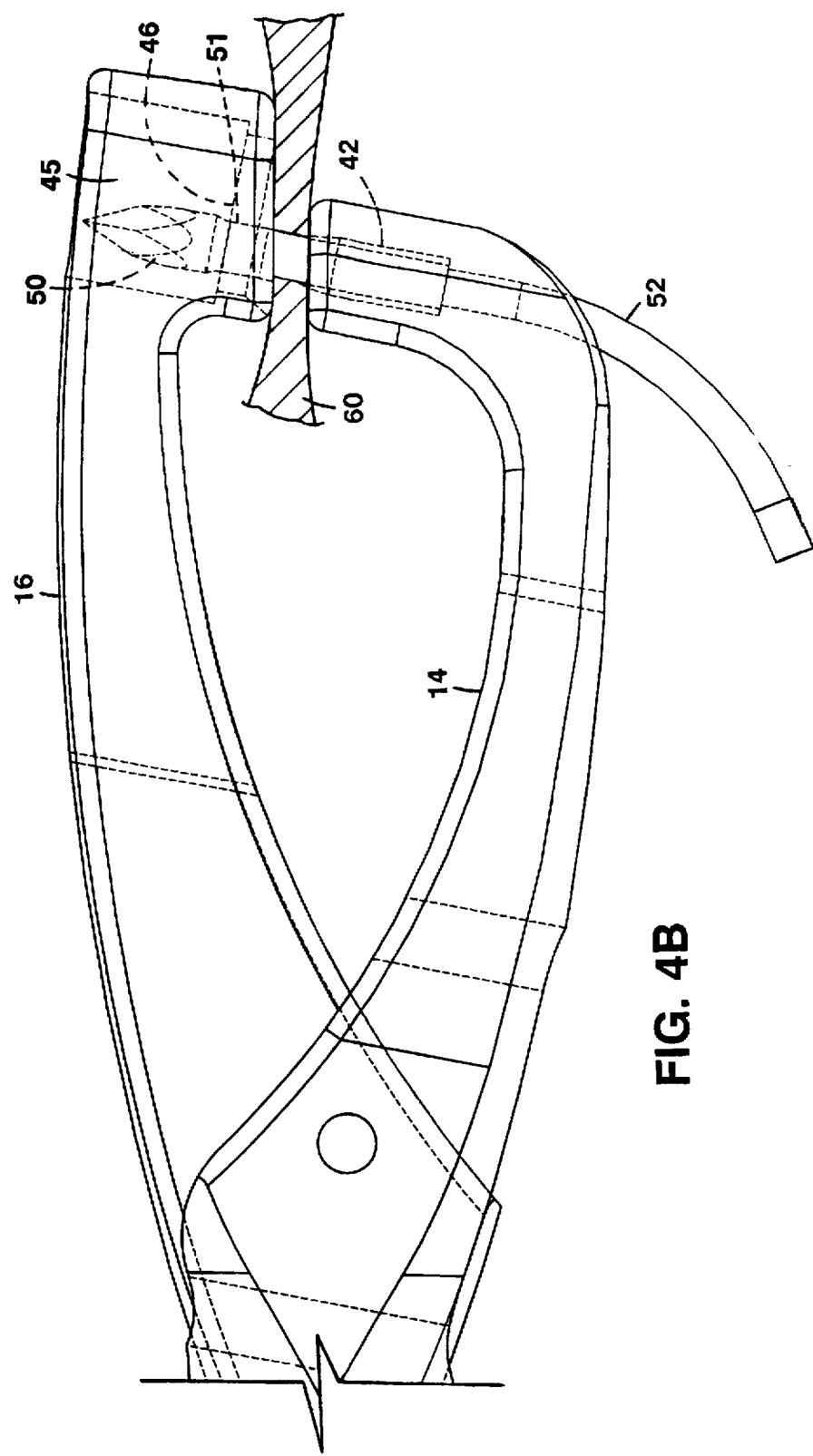
FIG. 4B shows the suturing assembly of FIG. 4 in a second operating position.
Figure 4C:
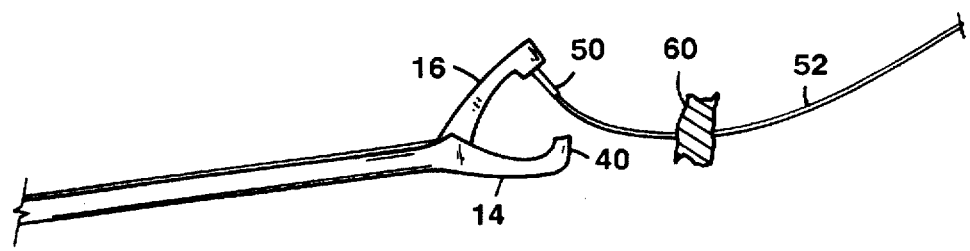
FIG. 4C shows the suturing assembly of FIG. 4 after the needled suture has been passed through tissue.

Referring to FIGS. 4–4C, in use needle 50 of needled suture 30 is placed in suture holding region 42 by passing thread 52 through slot 40 and pulling on thread 52 to place needle 50 within holding region 42. Handle 18 is actuated moving actuatable member 16 to the operating position shown in FIG. 4B, as needle 50 is pushed through the tissue 60 to be sutured. Closing of actuatable member 16 results in distal tip 54 of needle 50 being held within holding region 46 of actuatable member 16 (FIG. 4B). Due to the greater holding force of holding region 46 of actuatable member 16 as compared to the holding force of holding region 42 of suture holder 14, when actuatable member 16 is moved to its open position, needle 50 is passed from suture holder 14 to actuatable member 16 (FIG. 4C). Suture thread 52 is then free to pass through slot 40 to completely remove needled suture 30 from suture holder 14. Needle 50 can be pulled free from actuatable member 16 and suture thread 42 can then be cut and tied off.

Among the many advantages of the present suturing technique are passive capture of the needle within the holding regions, one-step suture passing, one-handed suturing action and complete removal of the needled suture from the suture holder after suture passing.

Figure 5:
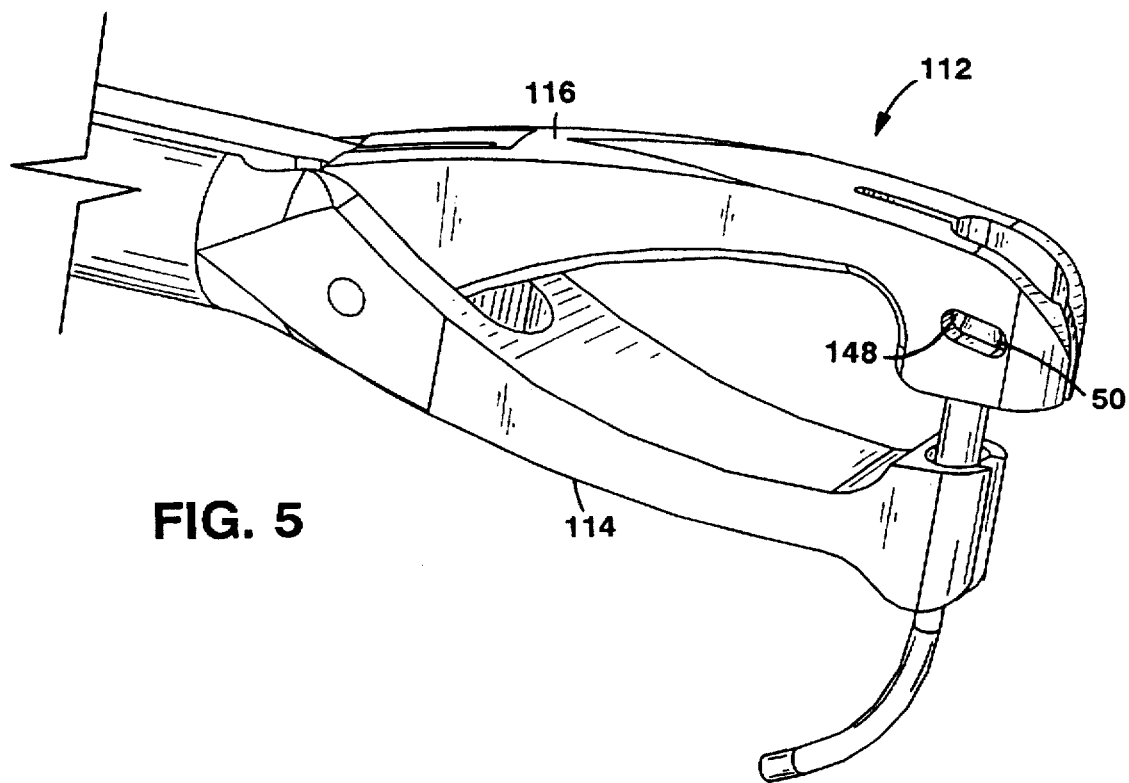
FIG. 5 shows an alternative embodiment of the suturing assembly of the suture passing forceps of the invention.

Referring to FIG. 5, in an alternative and preferred embodiment, suturing assembly 112 includes an actuatable member 116 having a window 148 through which needle 50 can be seen. Window 148 enables a user to confirm that the needle has been passed from suture holder 114 to actuatable member 116.

Figure 6:
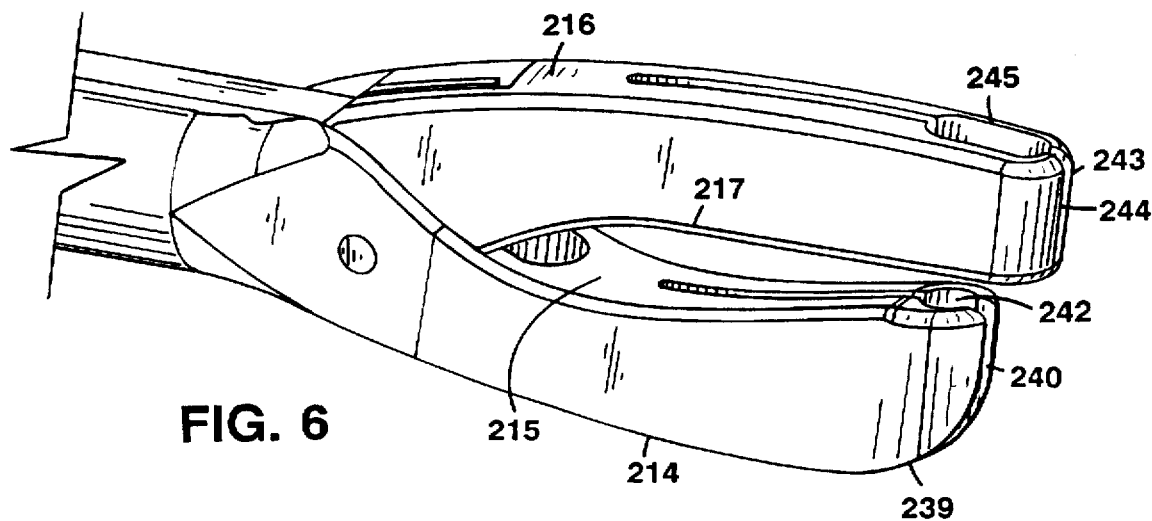
FIG. 6 shows another alternative embodiment of the suturing assembly of the suture passing forceps of the invention.

Referring to FIG. 6, in an alternative embodiment, suture holder 214 and actuatable member 216 include inner surfaces 215, 217, respectively, that aid in preventing tissue hang-up during removal of the suture passing forceps after needled suture 30 has been passed from suture holder 214 to actuatable member 216, as described above. Suture holder 214 includes a jaw 239 with a suture inlet slot 240 and a needle holding region 242 for removably holding a needle. Actuatable member 216 includes a jaw 243 with a slot 244 with an enlarged section 245 defining a needle holding region, as discussed above.

Figure 7:
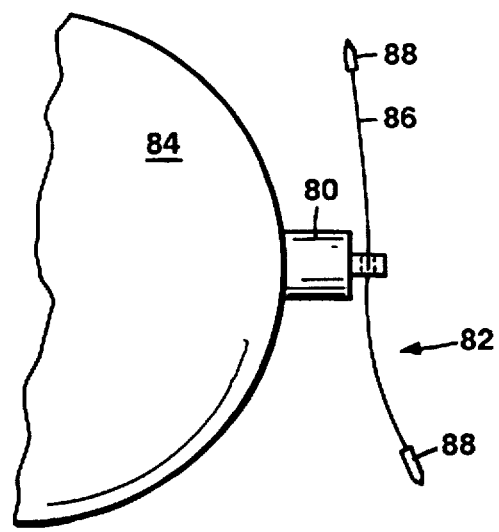
FIG. 7 shows an anchoring suture for use with the suture passing forceps of the invention.

Referring to FIG. 7, the suture passing forceps of the invention can be used with a suture anchor 80 for attachment to bone 84. A needled suture 82 passes through an opening of anchor 80. Needled suture 82 includes a suture thread 86 and a substantially straight, tubular-shaped, sharp-tipped needle 88, corresponding to needle 50 of FIG. 3, attached to one or both ends of suture thread 86.

In use during minimally-invasive suturing of deep tissue through a portal, suture thread 86 with needles 88 is passed through suture anchor 80, and, optionally, tied or crimped to suture anchor 80. A first tissue is sutured using one of the needled ends of suture thread 86 and a second tissue is sutured using the other needled end of suture thread 86. During both suturing steps, suture thread 86 is always passing through suture anchor 80.

Figure 8:
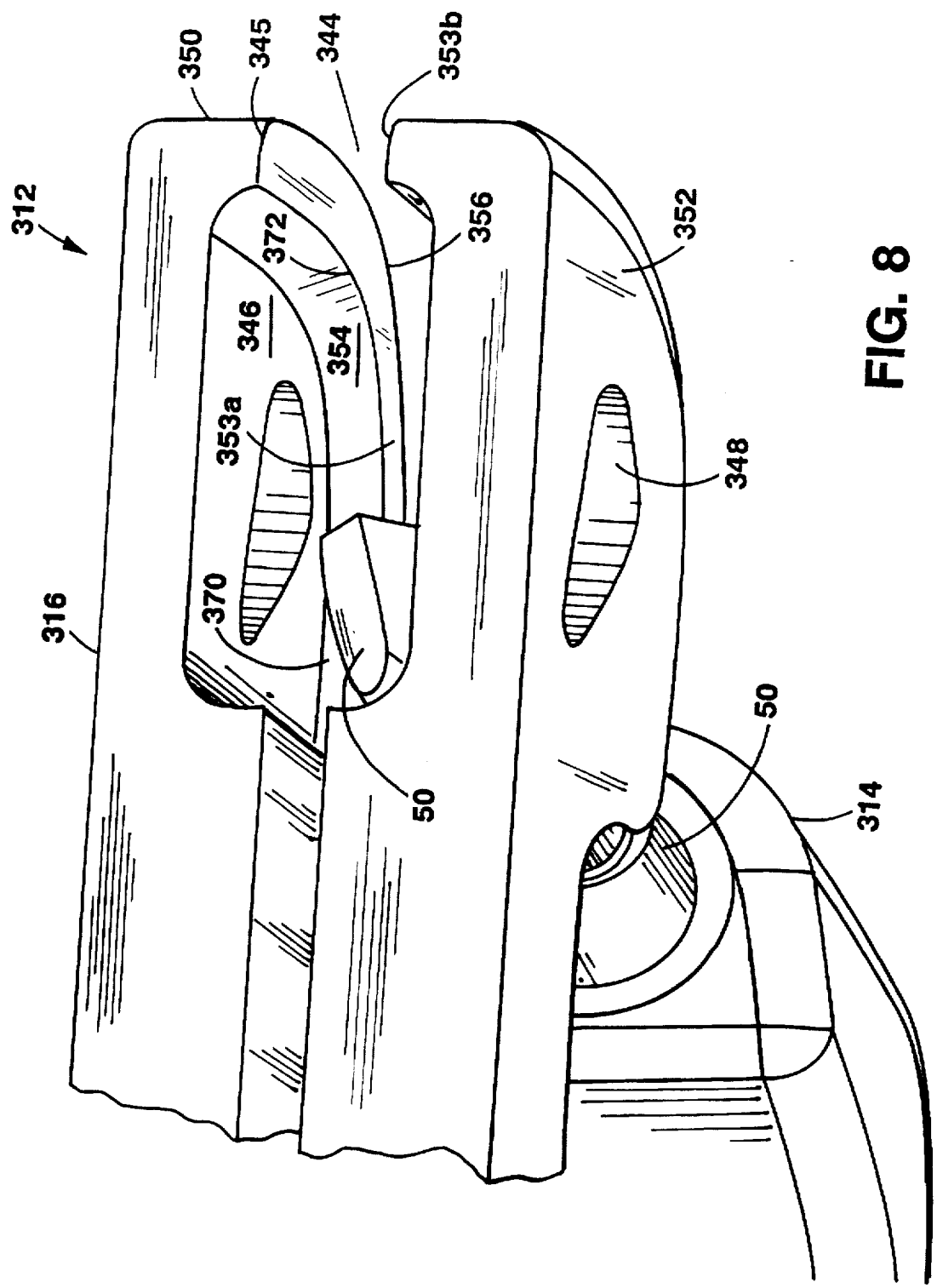
FIG. 8 shows another alternative embodiment of the suturing assembly of the suture passing forceps of the invention.

Referring to FIGS. 8–8C, in an alternative and preferred embodiment, a suturing assembly 312 includes an actuatable member 316 having a window 348 through which needle 50 can be seen. Window 348 enables a user to confirm that the needle has been passed from a suture holder 314 to actuatable member 316. Actuatable member 316 includes first and second member halves 350, 352 having contoured inner surfaces 354 defining a needle holding region 346, and corresponding contoured outer surfaces 356 (only the contoured surfaces of member half 350 being shown). Needle holding region 346 may be created, for example, using electrical discharge machining using a ram shaped to create contoured inner surfaces 354. Halves 350, 352 define an open slot 344 between them into which needle 50 enters and is retained.

Figure 8A:
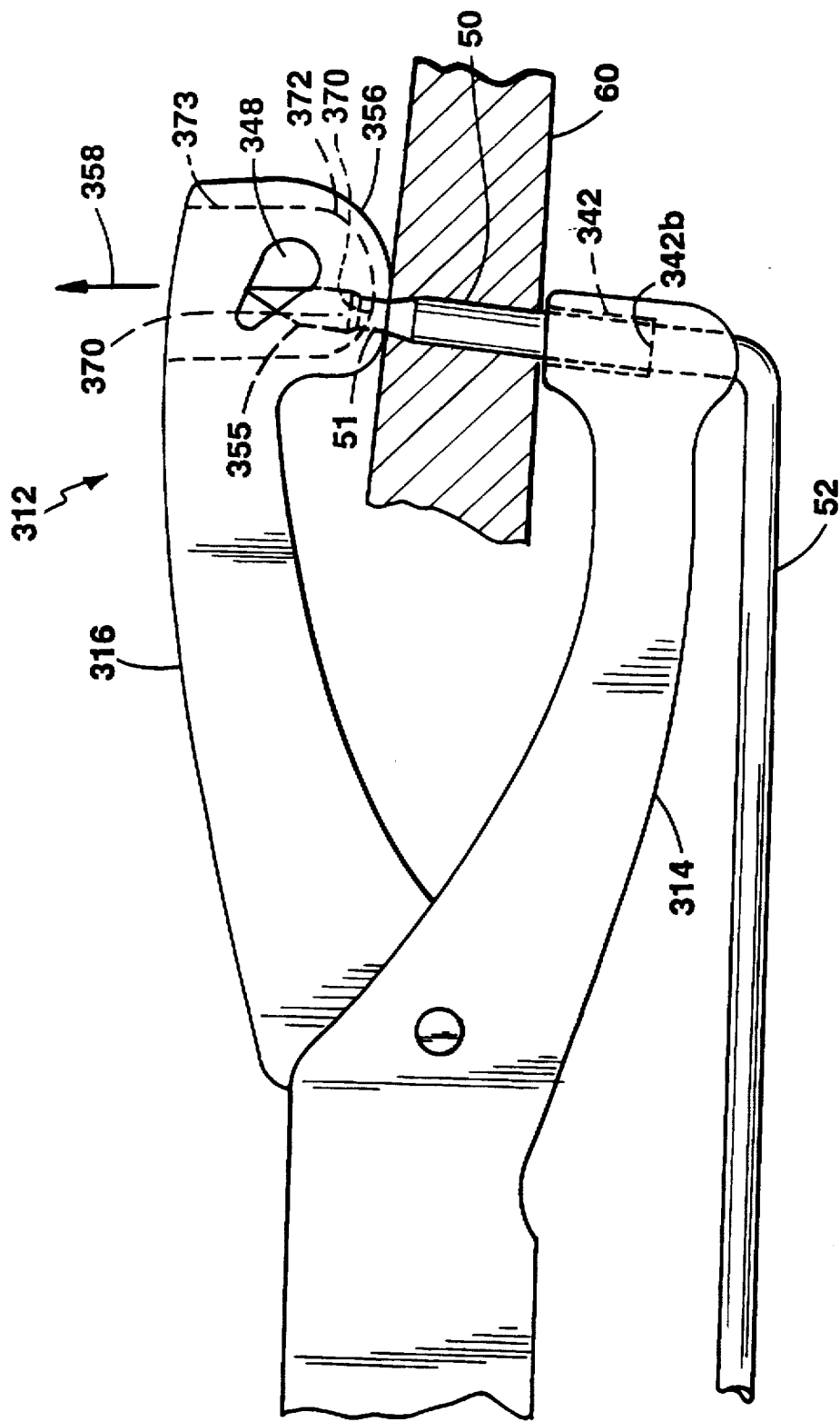
FIG. 8A shows the suturing assembly of FIG. 8 in a first operative position.

Referring particularly to FIGS. 8A and 8B, needle 50 is passed through tissue 60 and initially is retained by actuatable member 316, as described previously. In this preferred embodiment of the invention, the needle is held, in a passive spring fit, between halves 350, 352 at the edges 353a, 353b (FIG. 8) along a relatively flat region 370 of inner surfaces 354. It is the suture thread attachment area 51 of needle 50 which has a smaller diameter than a leading section 355 of the needle that is located between edges 353a, 353b. The actuatable member 316 is opened (moved in the direction of arrow 358), and the entire suturing assembly 312 is pulled away from tissue 60 releasing suture thread 52 from suture holder 314 and pulling suture thread 52 through tissue 60.

During the opening motion of actuatable member 316, needle 50 advantageously slides within suture holding region 346 along slot 344 allowing needle 50 to align with the suture thread as the thread tugs on the needle. Contoured inner surfaces 354, and particularly contoured region 372, allow the needle to slide within holding region 346 without creating any undesirable loads between needle 50 and member halves 350, 352 which may tend to pull needle 50 from the suture holding region. Additionally, contoured region 372 facilitates removal of needle 50 from actuating member 316 by guiding attachment area 51 of needle 50 in the direction of arrow 360. Needle 50 is guided along inner surfaces 354 of actuating member 316 and exits from the top 345 (FIG. 8) of slot 344 by appropriate manipulation of actuatable member 316 and needled suture 30.

It is desirable that the radius of contoured region 372 be as large as possible while still preserving a length of flat region 370 that is long enough, for example about 0.04", to initially capture needle 50.

Referring to FIGS. 8A and 8C, suture holder 314 includes an enlarged holding region 342 with a needle holding ledge 342b against which needle 50 rests when positioned in suture holder 314. A slot 340 extends from an external surface 314a of suture holder 314 to enlarged region 342.

Additions, subtractions and other modifications of the illustrated embodiments of the invention will be apparent to those practiced in the art and are within the scope of the following claims.

What is claimed is:

1. A suture passing forceps, comprising:

an axially elongated support shaft, and a suturing assembly at a distal end of said support shaft, including a first suture holder supported by said support shaft for removably holding a needled suture, said first suture holder including a suture inlet through which at least part of the suture can be passed, and a second suture holder supported by said support shaft for passively capturing said needled suture, said second suture holder including a holding region having a spring force for removably holding a needle of the needled suture, said holding region partially defined by a ledge extending along the holding region and configured to permit the held needle to slide, in a plane substantially transverse to a longitudinal axis of the needle, in a pivoting manner within the holding region, one of said first suture holder and said second suture holder being an actuatable member pivotably supported for movement toward and away from an operating position to passively capture said needled suture in said second suture holder as the actuatable member moves toward the operating position, and to remove the needled suture from said first suture holder when said actuatable member moves away from said operating position, said suture inlet in said first suture holder enabling complete removal of the suture from said first suture holder when said actuatable member and said needled suture move away from said operating position.

2. The suture passing forceps of claim 1 wherein said second suture holder comprises said actuatable member.

3. The suture passing forceps of claim 1 wherein said first suture holder includes a holding region for removably holding a needle of the needled suture.

4. The suture passing forceps of claim 3 wherein said first suture holder includes a jaw and said suture inlet is defined by a slot of a selected width in said jaw through which a suture thread of the needled suture can pass, said holding region being defined by an enlarged section of said slot into which the needle of the needled suture can be placed.

5. The suture passing forceps of claim 4 wherein said holding region is oriented at an angle of about 90 degrees to an axis of said support shaft.

6. The suture passing forceps of claim 4 wherein said enlarged section of said slot is oriented to hold the needle at an outward angle of about 5 to 10 degrees to an axis normal to a longitudinal axis of the support shaft.

7. The suture passing forceps of claim 1 wherein said holding region defines a passive spring fit.

8. The suture passing forceps of claim 1 wherein said second suture holder includes a jaw defining a slot of a selected width, said holding region being defined by an enlarged section of said slot into which at least a portion of the needle can be spring fit, the relative sizes of said needle and said enlarged section of said holding region defining, in part, said spring force.

9. The suture passing forceps of claim 1 further including a handle at a proximal end of said support shaft, said handle being actuatable to move said actuatable member toward and away from its operating position.

10. The suture passing forceps of claim 1 wherein said second suture holder further comprises a window enabling a user to confirm that the suture has been passed from said first suture holder to said second suture holder.

11. The suture passing forceps of claim 1 wherein said first and second suture holders include inner surfaces that aid in preventing tissue hang-up thereon.

12. A suture passing forceps, comprising:

an axially elongated support shaft, and a suturing assembly at a distal end of said support shaft, including a suture holder supported by said support shaft and including a jaw and a suture inlet defined by a slot of a selected width in said jaw through which a suture thread of the needled suture can pass, and a holding region defined by an enlarged section of said slot for removably holding a needle of a needled suture, and an actuatable member pivotably supported for movement toward and away from an operating position to passively capture said needled suture as the actuatable member moves toward the operating position, and to remove the needled suture from said suture holder when said actuatable member moves away from said operating position, said suture inlet in said suture holder enabling complete removal of the suture from said suture holder when said actuatable member and said needled suture move away from said operating position, said actuatable member including a jaw defining a slot of a selected width, a second holding region being defined by an enlarged section of said slot into which at least a portion of the needle can be spring fit, the relative sizes of said needle and said enlarged section of said holding region defining, in part, a spring force, said holding region including a ledge extending along the holding region and configured to permit the needled suture to slide, in a plane substantially transverse to a longitudinal axis of the needle, in a pivoting manner within said second holding region.

13. A suture passing forceps for passing a needled suture, comprising:

an axially elongated support shaft, and a suturing assembly at a distal end of said support shaft; including a first suture holder supported by said support shaft for removably holding a needled suture, said first suture holder including a suture inlet through which at least part of the suture can be passed, and a second suture holder supported by said support shaft for passively capturing said needled suture, one of said first suture holder and said second suture holder being an actuatable member pivotably supported for movement toward and away from an operating position to passively capture said needled suture in said second suture holder as the actuatable member moves toward the operating position, and to remove the needled suture from said first suture holder when said actuatable member moves away from said operating position, said suture inlet in said first suture holder enabling complete removal of the suture from said first suture holder when said actuatable member and said needled suture move away from said operating position, said second suture holder including a holding region defined by a ledge, said ledge extending along the holding region and configured to permit the needled suture to slide, in a plane substantially transverse to a longitudinal axis of the needle, in a pivoting manner with said holding region, said needled suture comprising:

a suture thread, and a sharp-tipped needle attached to a least one end of said suture thread, said needle having a substantially straight body co-axially aligned with said suture thread, said body including a holding portion having a different cross-sectional profile than portions of said body surrounding said holding portion.

14. A suture passing forceps, comprising:

an axially elongated support shaft, and a suturing assembly at a distal end of said support shaft, including a first suture holder supported by said support shaft for removably holding a needled suture, said suture holder including a suture inlet through which at least part of the suture can be passed, and a second suture holder supported by said support shaft for capturing said needled suture, one of said first suture holder and said second suture holder being an actuatable member pivotably supported for movement toward and away from an operating position to capture said needled suture in said second suture holder as the actuatable member moves toward the operating position, and to remove the needled suture from said first suture holder when said actuatable member moves away from said operating position, said second suture holder including a holding region partially defined by a ledge, said ledge extending along the holding region and configured to permit the needled suture to slide, in a plane substantially transverse to a longitudinal axis of the needle, in a pivoting manner within said holding region.

15. The suture passing forceps of claim 14 wherein said second suture holder comprises said actuatable member.

16. The suture passing forceps of claim 14 wherein said edge is configured to facilitate removal of said needled suture from said holding region.

17. The suture passing forceps of claim 14 wherein said second suture holder passively captures said needled suture.

18. The suture passing forceps of claim 17 wherein said holding region has a spring force for removably holding a needle of the needled suture.

19. The suture passing forceps of claim 18 wherein said holding region defines a passive spring fit.

20. The suture passing forceps of claim 19 wherein said second suture holder includes a jaw defining a slot of a selected width, said holding region being defined by an enlarged section of said slot into which the needle can be spring fit, the relative sizes of said needle and said enlarged section of said holding region defining, in part, said spring force.

21. The suture passing forceps of claim 14 wherein said suture inlet in said first suture holder enables complete removal of the suture from said first suture holder when said actuatable member and said needled suture move away from said operating position.

22. The suture passing forceps of claim 14 wherein said first suture holder includes a jaw and said suture inlet is defined by a slot of a selected width in said jaw through which a suture thread of the needled suture can pass, a needle holding region being defined by an enlarged section of said slot, a first portion of said enlarged section having a diameter greater than a diameter of the needle of the needled suture and a second portion of said enlarged section having a diameter less than the diameter of the needle.

23. The suture passing forceps of claim 22 wherein said slot is of limited depth extending from a surface of said jaw to said enlarged section.

24. A suture passing forceps for passing a needled suture, comprising:

an axially elongated support shaft, and a suturing assembly at a distal end of said support shaft, including a first suture holder supported by said support shaft for removably holding a needled suture, said suture holder including a suture inlet through which at least part of the suture can be passed, and a second suture holder supported by said support shaft for capturing said needled suture, one of said first suture holder and said second suture holder being an actuatable member pivotably supported for movement toward and away from an operating position to capture said needled suture in said second suture holder as the actuatable member moves toward the operating position, and to remove the needled suture from said first suture holder when said actuatable member moves away from said operating position, said second suture holder including a holding region defined by a ledge, said ledge extending along the holding region and configured to permit the needled suture to slide, in a plane substantially transverse to a longitudinal axis of the needle, in a pivoting manner within said holding region, said needled suture comprising:

a suture thread, and a sharp-tipped needle attached to a least one end of said suture thread, said needle having a substantially straight body co-axially aligned with said suture thread, said body including a holding portion having a different cross-sectional profile than portions of said body surrounding said holding portion.

* * * * *

UNITED STATES PATENT AND TRADEMARK OFFICE
CERTIFICATE OF CORRECTION

PATENT NO. : 5,730,747
DATED : March 24, 1998
INVENTOR(S) : Ek et al.

It is certified that error appears in the above-identified patent and that said Letters Patent is hereby corrected as shown below:

On the title page, add Paul Alec Torrie as an inventor.

In the References cited section, U.S. Patent No. 3,013,559, the correct date is 12/1961.

Col. 2, line 17, replace "a" with --at--.

Col. 8, claim 13, line 34, after "shaft" replace the semi-colon with a comma.

Col. 8, claim 13, line 62, replace "a" with --at--.

Col. 9, claim 16, line 29, replace "edge" with --ledge--.

Signed and Sealed this

Fourth Day of May, 1999

Attest:

Q. TODD DICKINSON

*Attesting Officer*     *Acting Commissioner of Patents and Trademarks*